US011654191B2

United States Patent
Sno et al.

(10) Patent No.: US 11,654,191 B2
(45) Date of Patent: May 23, 2023

(54) VACCINE FOR INTRADERMAL APPLICATION AGAINST PCV2 AND PRRS VIRUS INFECTION

(71) Applicant: Intervet Inc., Madison, NJ (US)

(72) Inventors: Melanie Sno, Venlo (NL); Maarten Hendrik Witvliet, Oostrum (NL); Vicky Fachinger, Bad Soden (DE)

(73) Assignee: Intervet Inc., Madison, NJ (US)

( * ) Notice: Subject to any disclaimer, the term of this patent is extended or adjusted under 35 U.S.C. 154(b) by 667 days.

(21) Appl. No.: 16/086,701

(22) PCT Filed: Mar. 22, 2017

(86) PCT No.: PCT/EP2017/056781
§ 371 (c)(1),
(2) Date: Sep. 20, 2018

(87) PCT Pub. No.: WO2017/162720
PCT Pub. Date: Sep. 28, 2017

(65) Prior Publication Data
US 2019/0099480 A1    Apr. 4, 2019

(30) Foreign Application Priority Data

Mar. 23, 2016    (EP) .................................. 16161994

(51) Int. Cl.
*A61K 39/12*    (2006.01)
*A61K 9/00*     (2006.01)
(Continued)

(52) U.S. Cl.
CPC ............ *A61K 39/12* (2013.01); *A61K 9/0021* (2013.01); *A61K 39/0241* (2013.01);
(Continued)

(58) Field of Classification Search
None
See application file for complete search history.

(56) References Cited

U.S. PATENT DOCUMENTS 6,217,883 B1    4/2001  Allan et al.
8,728,487 B2    5/2014  Wu et al.
(Continued)

FOREIGN PATENT DOCUMENTS

| CN | 101980720 A | 2/2011 |
| CN | 104334186 A | 2/2015 |

(Continued)

OTHER PUBLICATIONS

Extended European Search Report for U.S. Appl. No. 16/161,994 dated Sep. 29, 2016.
(Continued)

*Primary Examiner* — Shanon A. Foley
(74) *Attorney, Agent, or Firm* — Sarah L. Hooson; Catherine D. Fitch (57) ABSTRACT

The present invention pertains to a vaccine comprising in combination non-replicating immunogen of porcine circo virus type 2 and live attenuated PRRS virus for use in prophylactically treating an animal against an infection with porcine circovirus type 2 (PCV2) and an infection with PRRS virus by administration of the vaccine into the dermis of the animal.

9 Claims, 6 Drawing Sheets

(51) Int. Cl.
*A61K 39/02* (2006.01)
*A61K 39/00* (2006.01)

(52) U.S. Cl.
CPC ............... *A61K 2039/521* (2013.01); *A61K 2039/5254* (2013.01); *A61K 2039/54* (2013.01); *A61K 2039/70* (2013.01); *C12N 2750/10034* (2013.01); *C12N 2770/10034* (2013.01)

(56) References Cited

U.S. PATENT DOCUMENTS

| | | | |
|---|---|---|---|
| 2008/0181910 A1* | 7/2008 | Roof | A61K 39/12 424/204.1 |
| 2011/0150770 A1* | 6/2011 | Bautista | A61K 39/125 424/9.2 |
| 2013/0266602 A1 | 3/2013 | Nitzel | |

FOREIGN PATENT DOCUMENTS

| | | |
|---|---|---|
| CN | 104271153 B | 8/2018 |
| JP | 2002504317 A | 2/2002 |
| WO | 1999039582 A1 | 8/1999 |
| WO | 2005009462 A2 | 2/2005 |
| WO | 2006074986 A2 | 7/2006 |
| WO | 2007028823 A1 | 3/2007 |
| WO | 2007076520 A2 | 7/2007 |
| WO | 2007094893 A2 | 8/2007 |
| WO | 2008076915 A2 | 6/2008 |
| WO | 2009126356 A2 | 10/2009 |
| WO | 2009127684 A1 | 10/2009 |
| WO | 2013152086 A1 | 10/2013 |
| WO | 2014048955 A1 | 4/2014 |
| WO | 2015082457 A1 | 6/2015 |
| WO | 2015082458 A1 | 6/2015 |
| WO | 2015124594 A1 | 8/2015 |

OTHER PUBLICATIONS

Himmler, C et al., Comparison of reproductive parameters in sows vaccinated intradermally or intramuscularly with a modified live porcine reproductive and respiratory syndrome virus (PRRSV) vaccine, in consideration of parity and season, : Database Biosis (online); Biosciences Information Service, 2013, TIERAERZILICHE UMSCHAU, 61-65; BIOSIS XP002761605, 68(3).
International Search Report for appl. PCTEP2017056781 dated Jun. 12, 2017, 5 pages.

* cited by examiner

VACCINE FOR INTRADERMAL APPLICATION AGAINST PCV2 AND PRRS VIRUS INFECTION

CROSS-REFERENCE TO RELATED APPLICATIONS

This application is a national stage entry under 35 U.S.C. § 371 of PCT/EP2017/056781 filed on Mar. 22, 2017, which claims priority to EP16161994.5 filed on Mar. 23, 2016, the contents of which are hereby incorporated by reference in their entireties.

GENERAL FIELD OF THE INVENTION

The invention in general pertains to the field of swine health. Swine are prone to many pathogenic micro-organisms. Control of infection is commonly done by stable and feed management, treatment with pharmaceuticals such as anti-viral drugs and antibiotics, or prophylactic treatment using vaccines. In particular, the invention pertains a vaccine against porcine circo virus type 2 (PCV-2) and PRRS (porcine reproductive and respiratory syndrome) virus, and to a method of protecting an animal against such infections using the vaccine.

BACKGROUND ART

PCV2 and PRRS virus are two viruses that give rise to significant economic losses in the swine industry. PCV-2 is linked to the post-weaning multisystemic wasting syndrome (PMWS) observed in young pigs. This disease was encountered for the first time in Canada in 1991. The clinical signs and pathology were published in 1996, and include progressive wasting, dyspnea, tachypnea, and occasionally icterus and jaundice. Nayar et al., Can. Vet. J. Volume 38, June 1997 detected porcine circo virus in pigs with clinical symptoms of PMWS and concluded that a PCV, other than the known PCV recognized as a natural inhabitant of PK-15 cells, could be linked to PMWS. Later publications (Hamel et al., J.Virol., 72(6), 5262-5267, 1998; Meehan et al., J. gen.Virol., 79, 2171-2179, 1998) confirmed these findings, and it was proposed (Meehan et al., supra) to refer to the new pathogenic PCV as PCV-2, whereas the original PK-15 cell culture isolate (Tischer et al., Nature 295, 64-66, 1982), should be referred to as PCV-1. PCV-2 is a small (17-22 nm) icosahedral non-enveloped virus containing a circular single stranded DNA genome. The length of the PCV-2 genome is about 1768 bp. PCV-2 isolates originating from different regions in the world seem to be closely related to each other and display 95 to 99% nucleotide sequence identities (Fenaux et al., J.Clin. Micorbiol., 38(7), 2494-2503, 2000). ORF-2 of PCV encodes the capsid protein of the virus. The ORF 2 of PCV 2 encodes a protein of about 233 amino acids. The ORF 2 of all PCV-2 isolates share 91-100% nucleotide sequence identity and 90-100% deduced amino acid sequence identity.

PRRS virus first reported in 1987 in North America and Central Europe. PRRS virus is a small, enveloped RNA virus. It contains a single-stranded, positive-sense, RNA genome with a size of approximately 15 kilobases. The genome contains nine open reading frames. The virus is a member of the genus Arterivirus, family Arteriviridae, order Nidovirales. The two prototype strains of PRRSV are the North American strain, VR-2332, and the European strain, the Lelystad virus (LV). The European and North American PRRSV strains cause similar clinical symptoms. In the early 2000s a highly pathogenic strain of the North American genotype emerged in China. This strain, HP-PRRSV, is more virulent than all other strains, and causes great losses in Asian countries worldwide. For any PRRS virus, subclinical infections are common, with clinical signs occurring only sporadically in a herd. Clinical signs include reproductive failure in sows such as abortions and giving birth to stillborn or mummified fetuses, and cyanosis of the ear and vulva. In neonatal pigs, the disease causes respiratory distress, with increased susceptibility to respiratory infections such as Glässer's disease.

Vaccines against the above identified pathogens are commonly known. A conventional vaccine to prophylactically treat animals, in particular pigs, against an infection with PCV 2, may be based on whole inactivated PCV-2 virus as a (non-replicating) immunogen. Also, in the art it has been shown that the ORF2 encoded capsid protein (e.g. when recombinantly expressed) is suitable as a subunit immunogen of porcine circo virus type 2 for use in an adequate vaccine. This can be understood since this subunit, in a circulatory system, shows up the same way as the virus itself, essentially differing in the fact that the DNA and non-structural proteins are not present inside the capsid. In the art several vaccines against PCV2 are commercially available. Porcilis® PCV (available from MSD Animal Health, Boxmeer, The Netherlands) is a vaccine for protection of pigs against porcine circo virus type 2, for use in pigs from three weeks and older. When given as a two-shot (two dose) vaccine, the duration of immunity (DOI) is 22 weeks, almost completely covering the fattening period of pigs. Ingelvac CicroFlex® (available from Boehringer Ingelheim, Ingelheim) is a vaccine for protection of pigs against porcine circo virus type 2, for use in pigs from two weeks and older. It is registered as a one-shot (one dose) vaccine only. Circovac® (available from Merial, Lyon, France) is a vaccine for protection of pigs against porcine circo virus type 2, for use in pigs three weeks and older. Suvaxyn® PCV (available from Zoeitis, Capelle a/d Ussel, The Netherlands) is a vaccine for protection of pigs against porcine circo virus type 2, for use in pigs from three weeks and older. Other PCV2 vaccines are described for example in WO2007/028823, WO 2007/094893 and WO2008/076915.

Regarding PRRS virus, although inactivated virus vaccines have been described and are commercially available, modified Live Vaccines (MLV) vaccines comprising either the European type (type I) or the North American type (type II) in live attenuated form, are the primary immunological tool for its control. Several vaccines are commercially available in the art. Porcilis® PRRS (available from MSD Animal Health, Boxmeer, The Netherlands) is a vaccine comprising live attenuated PRRS virus type I and is registered to reduce infection (viraemia) caused by infection with PRRS virus. Ingelvac PRRS® MLV (available from Boehringer Ingelheim, Ingelheim) is a vaccine that aids in the reduction of disease caused by PRRS virus and which vaccine provides cross protection against strains of different types. Fostera® PRRS (available from Zoeitis, Florham Park, N.J., USA) is also a MLV vaccine and is registered for protection against both the respiratory and reproductive forms of disease caused by PRRS virus. Other PRRS vaccines are described for example in WO2006/074986, U.S. Pat. No. 8,728,487 and WO2014/048955.

OBJECT OF THE INVENTION

There is a continuous need for convenient, safe and efficacious means for the management of swine health. The object of the invention is to provide a vaccine that meets this need, in particular the need for a novel PCV2/PRRS virus combination vaccine.

SUMMARY OF THE INVENTION

In order to meet the object of the invention, a new vaccine has been devised, the vaccine comprising in combination non-replicating immunogen of porcine circo virus type 2 and live attenuated PRRS virus for use in prophylactically treating an animal against an infection with porcine circovirus type 2 (PCV2) and an infection with PRRS virus by administration of the vaccine into the dermis of the animal.

Although for both viruses vaccines are known and commercially available, there is no combination vaccine available for intradermal administration, which vaccine is efficacious and at the same time safe for use in young animals. As is commonly known, not all combinations of antigens contemplated or suggested may lead to a safe and effective combination vaccine. In fact, there is a high level of uncertainty with regard to the stability, safety and efficacy of the combination vaccine, even when the single (monovalent) vaccines are safe and efficacious.

The committee for veterinary medicinal products of the European Agency for the Evaluation of Medicinal Products (EMEA) in its publication "Note for guidance: requirements for combined veterinary products" (EMEA, 2000, CVMP/IWP/52/97-FINAL), stated (page 2/6) that the "development of combined vaccines is not straightforward. Each combination should be developed and studied individually in terms of quality, safety and efficacy". The committee further indicates that the search for a good combination vaccine typically includes the compatibility between the individual components in the combined vaccine, including for example preservatives, excipients and stabilisers, inactivating agents and adjuvants. On page 3, top paragraph, it is stated that "In combined vaccines, the presence of more than one component can often cause an interaction, leading to either a diminished or an increased response to individual components, compared to when the specific component(s) is administered alone Such interactions are often immunological in nature, but may also be caused by other factors with less direct effects on the immune system", and also "When an adjuvant is used to augment the immune response to a combined vaccine, special problems may appear."

The U.S. Department of Health and Human Services, Food and Drug Administration, Center for Biologics Evaluation and Research, published in April 1997 a "Guidance for Industry, for the evaluation of combination vaccines for preventable diseases: Production, Testing and Clinical Studies", in which guidance it is stated (page 3, under "Compatibility of Components") that "Experience has shown that combining monovalent vaccines may result in a new combination which is less safe or effective than desirable. Sometimes the components of inactivated vaccines may act adversely on one or more of the active components", indicating that especially an inactivated vaccine may negatively influence the efficacy of a live vaccine, such as for example occurred when combining a live pertussis vaccine and an inactivated poliovirus vaccine that resulted in a vaccine with decreased pertussis potency. It is indicated that any additional components in the vaccine might complicate the safety and potency of the final product when compared to the individual vaccines.

The World Health Organization (WHO) has published an e-learning course called "Vaccine Safety Basics", which in the MODULE 2 contemplates combination vaccines. This module starts with "Licensed combination vaccines undergo extensive testing before approval by national authorities to assure that the products are safe, effective, and of acceptable quality." It is also stated that "With all combinations, manufacturers must therefore evaluate the potency of each antigenic component, the effectiveness of the vaccine components when combined to induce immunity, risk of possible reversion to toxicity, and reaction with other vaccine components."

It is thus not straightforward to devise a new combination vaccine, let alone a new vaccine for a particular site of administration. The World Health Organization (WHO) for example has published an e-learning course called "Vaccine Safety Basics", in which course on page 53 it is reported that "The route of administration is the path by which a vaccine (or drug) is brought into contact with the body. This is a critical factor for success of the immunization. A substance must be transported from the site of entry to the part of the body where its action is desired to take place. Using the body's transport mechanisms for this purpose, however, is not trivial."

In this respect the California Department of Health Services' Immunization Branch has published guidelines for correct immunization (www.cdc.gov/vaccines/pubs/pinkbook/downloads/appendices/d/vacc_admin.pdf). With regard to the administration site it is stated on page 7, first full paragraph that "The recommended route and site for each vaccine are based on clinical trials, practical experience and theoretical considerations. This information is included in the manufacturer's product information for each vaccine. There are five routes used in the administration of vaccines. Deviation from the recommended route may reduce vaccine efficacy or increase local adverse reactions." On page 14 the only US-licensed intradermal vaccine is addressed: "Fluzone Intradermal is the only U.S.-licensed vaccine that is administered by the intradermal route. It is approved only for use in persons 18 through 64 years of age. This Fluzone formulation is not the same as intramuscular formulations of inactivated influenza vaccine (TIV). Other TIV formulations should NOT be administered by the intradermal route."

All in all, it is commonly known that vaccination at a particular site, let alone vaccination of a combination vaccine at a particular site, is not straightforward and requires experimentation to determine safety and efficacy.

Regarding intradermal administration, although intradermal administration is often carried out using a needle-less vaccination device such as the IDAL® vaccinator (available from MSD Animal Health, Boxmeer, The Netherlands), "intradermal" administration per se should not be equated with "needle-less" administration. The World health Organization in its Aug. 27, 2009 paper titled "Intradermal Delivery of Vaccines; A review of the literature and the potential for development for use in low- and middle-income countries" indeed clearly indicates that "needle-less" vaccination does not necessarily mean "intradermal" vaccination (see Table 1, Page 3 of the review). Only when a needle-less device is "configured for intradermal vaccination", then a vaccine may indeed be delivered (at least partly) into the dermis. Otherwise the vaccine may be delivered subcutaneous or intramuscularly in its entirety.

The present invention also pertains to a method for prophylactically treating an animal against an infection with porcine circovirus type 2 (PCV2) and an infection with PRRS virus by intradermally administrating to the animal a vaccine comprising in combination non-replicating immunogen of PCV2 and live attenuated PRRS virus, and to the use of non-replicating immunogen of porcine circo virus type 2 (PCV2) and live attenuated PRRS virus to manufacture a vaccine comprising in combination the immunogen of PCV2 and the live attenuated PRRS virus for intradermal administration to an animal to prophylactically treat the animal against an infection with PCV2 and an infection with PRRS virus.

It is noted that in a vaccine the immunogen (also called antigen) is typically combined with a pharmaceutically acceptable carrier, i.e. a biocompatible medium, viz. a medium that after administration does not induce significant adverse reactions in the subject animal, capable of presenting the immunogen to the immune system of the host animal after administration of the vaccine, such as a liquid containing water and/or any other biocompatible solvent or a solid carrier such as commonly used to obtain freeze-dried vaccines (based on sugars and/or proteins), optionally comprising immunostimulating agents (adjuvants), which upon administration to the animal induces an immune response for treating an animal against an infection with a wild-type micro-organism, i.e. for aiding in preventing, ameliorating or curing such infection or a disorder arising therefrom. Optionally other substances such as stabilisers, viscosity modifiers or other components are added depending on the intended use or required properties of the vaccine.

Definitions

A vaccine is a pharmaceutical composition that is safe to administer to a subject animal, and is able to induce protective immunity in that animal against a pathogenic micro-organism, i.e. to induce a successful prophylactic treatment as defined here below.

Non-replicating immunogen of a pathogen is any substance or compound corresponding to the pathogen, other than the live replicating pathogen as a whole (either in wild type of attenuated form), against which pathogen an immunological response is to be elicited, such that the corresponding virulent pathogen or one or more of its virulence factors will be recognized by the host's immune system as a result of this immune response and are ultimately at least partly neutralized. Typical examples of non-replicating immunogens are killed whole pathogens and subunits of these pathogens such as capsid proteins and other surface expressed proteins, for example recombinantly expressed proteins.

Prophylactic treatment against an infection with a pathogen is aiding in preventing or ameliorating an infection with that pathogen or a disorder arising from that infection, resulting from a post treatment challenge with a pathogenic pathogen, in particular to reduce its load in the host after such challenge and optionally to aid in preventing or ameliorating one or more clinical manifestations resulting from the post treatment infection with the pathogen.

A live attenuated pathogen is a viable, replication competent form of the pathogen having reduced virulence. The process of attenuation takes an infectious pathogen and alters it so that it becomes harmless or less virulent, typically by either multiple passages of the pathogen through cell systems or by genetically modifying the pathogen.

Single dose administration of a vaccine for use in prophylactically treatment means that in order to arrive at protective immunity, the vaccination does not need to be boosted with a second administration of the vaccine. In a two-shot regime, the first (prime) vaccination is typically boosted within 6 weeks from the first administration, commonly within 3 or even 2 weeks from the first administration, and only after the second (boost) administration protective immunity, i.e. a successful prophylactic treatment as defined here above, may be obtained.

EMBODIMENTS OF THE INVENTION

In a first embodiment the vaccine is administered by a single dose. It was found that a single dose administration led to an effective vaccination. This provides for a very convenient and economical way to protect animals against both pathogenic viruses.

In a next embodiment the vaccine is administered with a needle-less vaccination device, using a jet of the vaccine to reach the dermis through the skin of the animal. Vaccination into the dermis is in this embodiment provided by a needle-less vaccination device using a liquid jet of the vaccine (a high pressurized fluid stream), typically using a very low volume of vaccine in the range of 0.05 to 0.2 ml. This further increases the safety of the vaccine and method of administration.

In another embodiment the non-replicating immunogen is recombinantly expressed ORF2 protein of porcine circo virus type 2, for example expressed by baculo virus as known in the art. This recombinant protein has proven to be suitable for application in the present invention. In particular, the ORF2 protein can be expressed in a baculo virus expression system such as described in WO2007/028823, WO 2007/094893 or WO2008/076915.

In yet another embodiment the immunogen of PCV2 and the live attenuated PRRS virus are combined in the vaccine within 24 hours, preferably within 6 hours before administration. Combining the antigens right before administration provides more freedom to choose the excipients since long-term stability, although known for many pharmaceutical compositions, even for combination vaccines including PCV2 ORF2 antigen (for example Porcilis® PCV M Hyo, available from MSD Animal Health), as such is known, might still not be straightforward to achieve, at least not for any and all pharmaceutically acceptable carrier compositions.

In still another embodiment the vaccine comprises in addition non-replicating immunogen of *Mycoplasma hyopneumoniae* (*M. hyo*) In this embodiment the vaccine is capable of providing protection against three major swine pathogens by using just one vaccine. Many commercial vaccines against *M.hyo* exist and these are routinely used in the majority of commercial swine farming operations. Generally these vaccines comprise non-replicating immunogens such as subunit proteins and/or bacterins (i.e. a composition comprising killed bacteria, either as whole cells, (partly) lysed, homogenised, French pressed, a combination of this or comprising the killed bacteria in another form as long as the composition is derived from a killed bacterial culture) which are typically administered by parenteral injection. Some examples are: RespiSure® (Zoetis), Ingelvac® *M. hyo*, and MycoFLEX® (Boehringer Ingelheim), Hyoresp® (Merial), Stellamune® Mycoplasma (Elanco Animal Health), Fostera® PCV MH (Zoetis) and M+Pac® (MSD Animal Health).

The invention will now be further explained using the following examples.

EXAMPLES

Study 1

Objective

The objective of the study is to evaluate efficacy and safety of live attenuated PRRS virus vaccine when dissolved in various PCV2 ORF2 vaccines, after intradermal administration. The efficacy towards protection against infection with PCV2 is evaluated by assessing anti-ORF2 serology (the anti-ORF2 antibodies are known to neutralize the PCV2 virus). The efficacy against an infection with PRRS virus is evaluated by assessing the PRRS viraemia upon challenge with a pathogenic PRRS strain, 4 weeks post vaccination.

Experimental design

The progeny of 10 sows was available for this study. A total of 50 animals were allotted to 5 groups of 10 piglets each. All animals were transferred to an animal facility when they were approximately 4 weeks old. Groups 1 to 4 were intradermally vaccinated using the IDAL® vaccinator into the right side of the neck. Groups 1 to 3 each received an ORF2 protein based PCV2 vaccine in which a live PRRS virus vaccine (Porcilis PRRS) is reconstituted. The various PCV2 vaccines originate from three different production runs. Each vaccine contained 9 µg of ORF2 protein per dose of the ORF2 protein (as compared to over 20 µg per dose in the commercially available Porcilis® PCV vaccine), and was based on the commercially available XSolve adjuvant (MSD Animal Health, Boxmeer, The Netherlands) to which 3% ovalbumin was added as a stabiliser. The PRRS vaccine was a freeze-dried vaccine and is reconstituted immediately before administration to contain $10^{4.5}$ $TCID_{50}$ of virus per dose of 200 µl using the appropriate PCV2 vaccine or a diluent. Group 4 only received the PRRS vaccine and group 5 remained unvaccinated and served as control. All piglets were observed daily for clinical signs. The animals were challenge-infected with pathogenic PRRS virus (type I) when they were approximately 8 weeks old (day 28). The challenge material contained (a calculated dose of) 5.3 log 10 $TCID_{50}$ of the virus in 2 ml. The material was intranasally administered, 1 ml per nostril. At the end of the observation period (49 days after vaccination corresponding to 21 days post challenge) all pigs were sacrificed. Blood samples (via v. jugularis) were taken from all animals individually on day 0, 14, 28 (right before challenge), 31, 35, 38, 42 and 49 and tested for the presence of PRRS virus, for antibodies against PRRSV and PCV2.

Results

No animals showed any clinical signs due to vaccination and rectal temperatures remained within 1.5° C. from controls. The vaccines are thus regarded safe.

Figure 1:
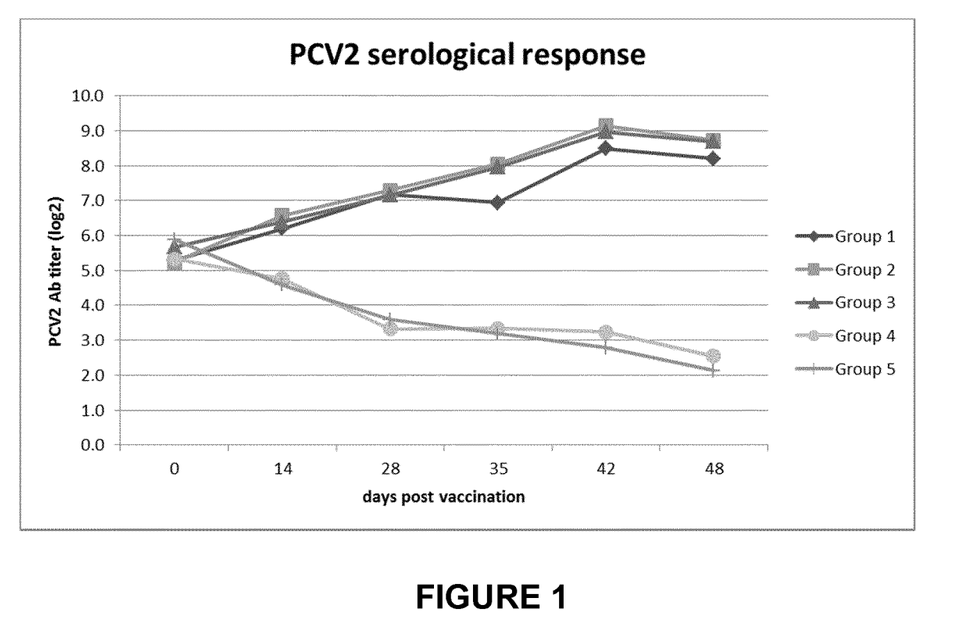

The results of the PCV2 serological response are given in FIG. 1. It appears that all combination vaccines induce a positive anti-ORF2 antibody response which means that the vaccines induce protective immunity against infection with wild-type PCV2.

Figure 2:
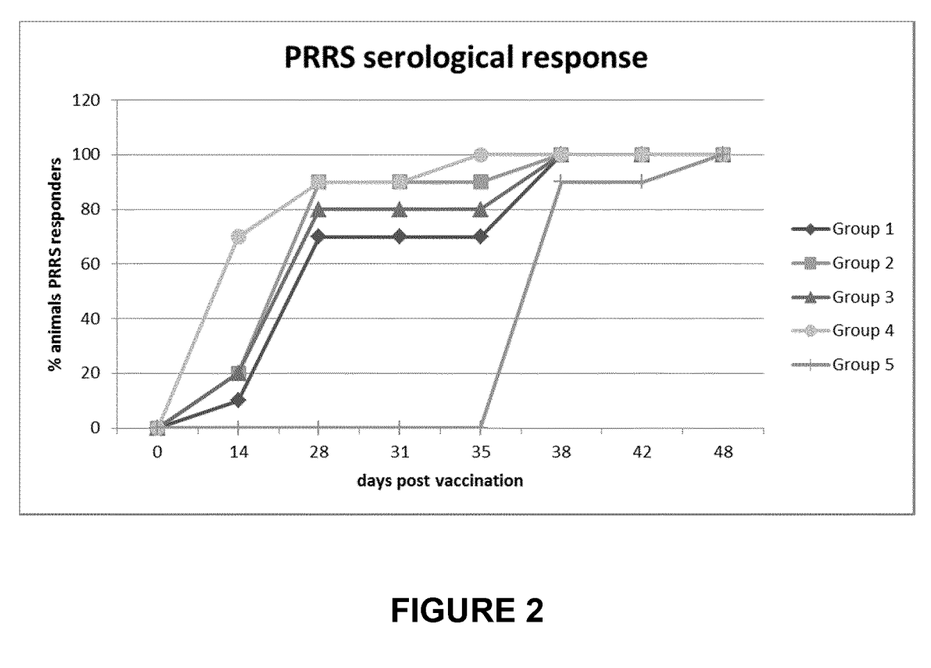
Figure 3:
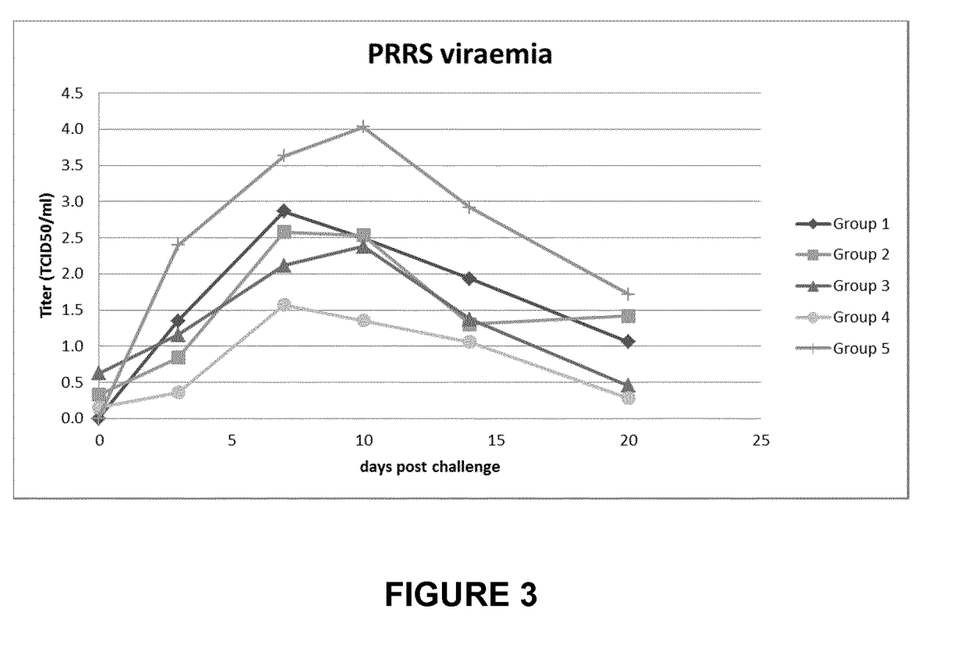

The results of the PRRS serological response are given in FIG. 2. It appears that all combination vaccines, like the commercially available PRRS vaccine, induce a positive anti-PRRS antibody response before challenge. This is an indication that the vaccines provide protection against PRRS virus infection. In FIG. 3 the viraemia data are given. It appears that all vaccines provide protection against PRRS virus infection since viraemia levels are lower than the level in the positive control animals (group 5) at each point in time.

Study 2

Objective

The objective of the second study is to evaluate efficacy and safety of live attenuated PRRS virus vaccine when dissolved in different PCV2/Mhyo combination vaccines, after intradermal administration. The efficacy towards protection against infection with PCV2 is evaluated by assessing anti-ORF2 serology. The efficacy against infection with *Mycoplasma hyopneumoniae* is evaluated by comparing the serological response with that of the commercially available Mhyo vaccine Porcilis® Mhyo (MSD Animal Health, Boxmeer, The Netherlands). The efficacy against an infection with PRRS virus is evaluated by assessing the PRRs viraemia upon challenge with a pathogenic PRRS strain, 4 weeks post vaccination.

Experimental Design

The progeny of 10 sows was available for this study. A total of 40 animals were allotted to 4 groups of 10 piglets each. All animals were transferred to an animal facility when they were approximately 4 weeks old. Groups 1 to 4 were intradermally vaccinated using the IDAL® vaccinator into the right side of the neck. Groups 1 and 2 each received an ORF2 protein based PCV2 vaccine comprising in addition Mhyo bacterin (the same as in Porcilis M Hyo), in which combination vaccine a live PRRS virus vaccine (Porcilis PRRS) was reconstituted. The vaccine for group 1 was based on a Montanide adjuvant (IMS 251, available from SEPPIC, France) to which 3% ovalbumin is added. The vaccine of group 2 contained the same adjuvant but no ovalbumin was added. Each vaccine contained 9 µg/dose of the ORF2 protein, and Mhyo antigen at twice the concentration of the M Hyo antigen in the commercially available vaccine Porcilis® M Hyo ID ONCE. The PRRS vaccine was a freeze-dried vaccine and was reconstituted immediately before administration to contain $10^{4.5}$ $TCID_{50}$ of virus per dose of 200 µl using the appropriate PCV2 vaccine or a diluent. Group 3 only received the PRRS vaccine and group 4 remained unvaccinated and served as control. All piglets were observed daily for clinical signs. The animals were challenge-infected with pathogenic PRRS virus (type I) when they were approximately 8 weeks old (day 28). The challenge material contained (a calculated dose of) 5.3 log 10 TCID50 of the virus in 2 ml. The material was intranasally administered, 1 ml per nostril. At the end of the observation period (49 days after vaccination corresponding to 21 days post challenge) all pigs were sacrificed. Blood samples (via v. jugularis) were taken from all animals individually on day 0, 14, 28 (right before challenge), 31, 35, 38, 42 and 49 and tested for the presence of PRRS virus, for antibodies against PRRSV, PCV2 and Mhyo.

Results

No animals showed any clinical signs due to vaccination and rectal temperatures remained within 1.5° C. from controls. The vaccines are thus regarded safe.

Regarding Mhyo, the serological response of the combination vaccine appears to be comparable to that as obtainable with the commercially available vaccine Porcilis M Hyo (no numerical results depicted in a figure). It may thus be concluded that the vaccine protects against infection with Mhyo.

Figure 4:
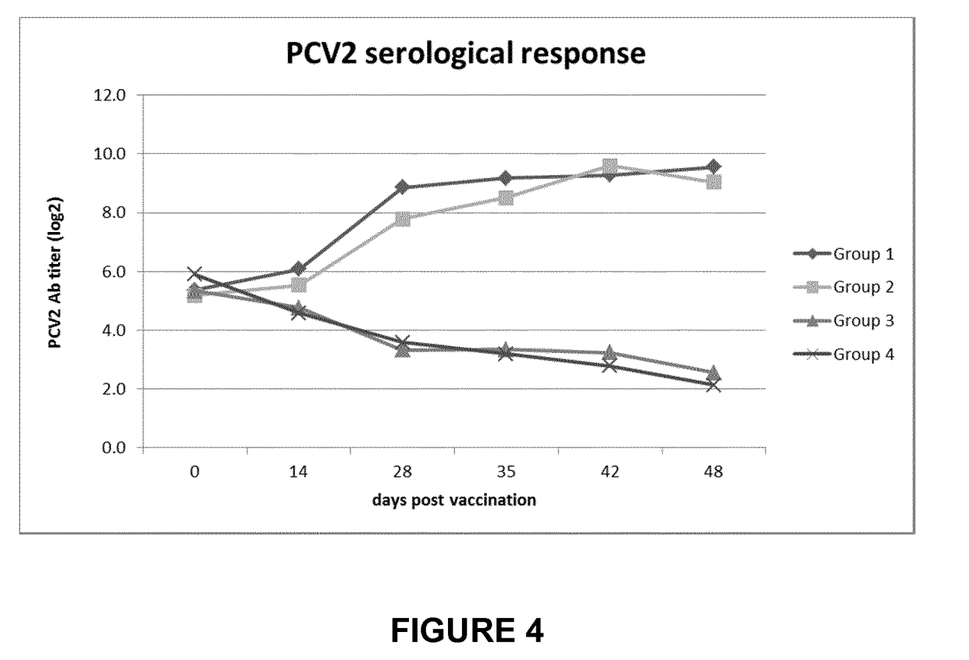

The results of the PCV2 serological response are given in FIG. 4. It appears that the two combination vaccines induce a positive anti-ORF2 antibody response which means that the vaccines induce protection against infection with wild-type PCV2.

Figure 5:
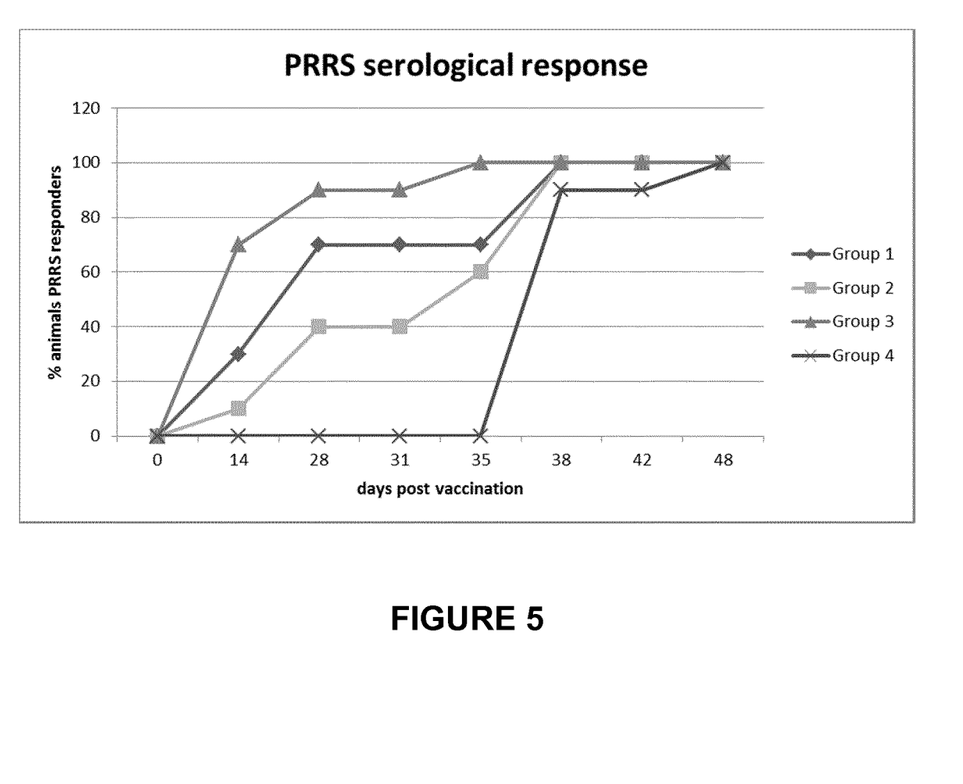
Figure 6:
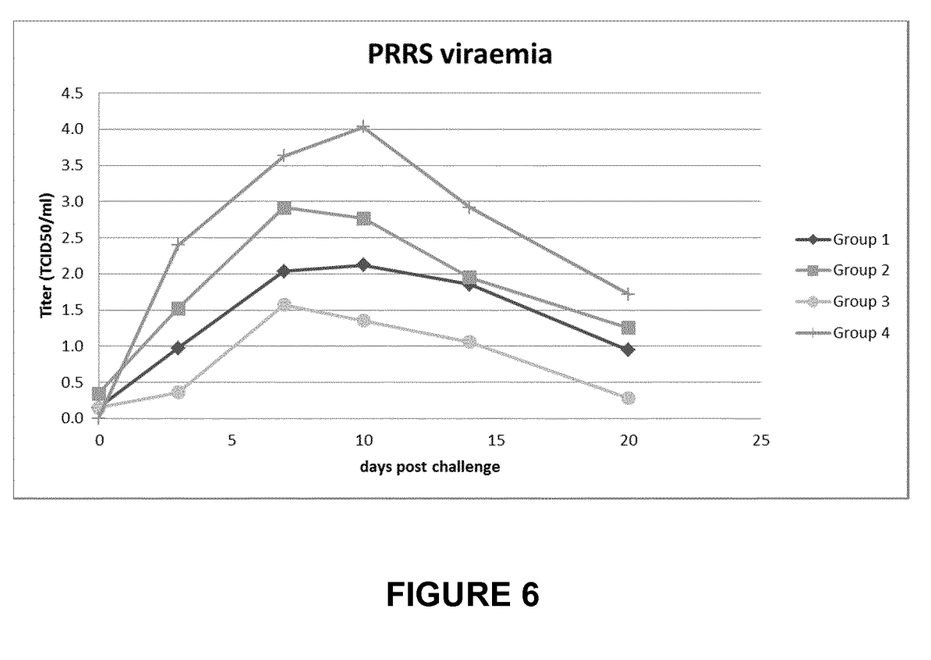

The results of the PRRS serological response are given in FIG. 5. It appears that the two combination vaccines, like the commercially available PRRS vaccine, induce a positive anti-PRRS antibody response before challenge. This is an indication that the vaccines provide protection against PRRS virus infection. In FIG. 6 the viraemia data are given. It appears that all three vaccines provide protection against PRRS virus infection since viraemia levels are lower than the level in the positive control animals (group 4) at each point in time.

The invention claimed is:

1. A single-dose vaccine comprising in combination a non-replicating immunogen of porcine circovirus type 2 (PCV2) and a live attenuated porcine reproductive and respiratory syndrome (PRRS) virus, wherein the vaccine is administered intradermally for use in prophylactically treating an animal against an infection of PCV2, PRRS virus, or both PCV2 and PRRS virus.

2. The vaccine of claim 1, wherein the vaccine is administered with a needle-less vaccination device.

3. The vaccine of claim 1, wherein the non-replicating immunogen of PCV2 is recombinantly expressed ORF2 protein of PCV2.

4. The vaccine of claim 1, wherein the non-replicating immunogen of PCV2 is baculovirus expressed ORF2 protein of PCV2.

5. The vaccine of claim 1, wherein the vaccine additionally comprises a non-replicating immunogen of *Mycoplasma hyopneumoniae*.

6. A method for prophylactically treating an animal against an infection with porcine circovirus type 2 (PCV2), an infection with porcine reproductive and respiratory syndrome (PRRS) virus, or an infection with both PCV2 and PRRS virus, by administrating into the dermis of the animal a vaccine comprising in combination a non-replicating immunogen of PCV2 and a live attenuated PRRS virus.

7. The method of claim 6, wherein the immunogen of PCV2 and the live attenuated PRRS virus are combined in the vaccine within 24 hours before administration.

8. The method of claim 6, wherein the immunogen of PCV2 and the live attenuated PRRS virus are combined in the vaccine within 6 hours before administration.

9. A method of manufacturing a vaccine comprising combining a non-replicating immunogen of porcine circovirus type 2 (PCV2) and live attenuated porcine reproductive and respiratory syndrome (PRRS) virus into one single-dose vaccine for intradermal administration to an animal to prophylactically treat the animal against an infection with PCV2, an infection with PRRS virus, or an infection of both PCV2 and PRRS virus.

* * * * *

UNITED STATES PATENT AND TRADEMARK OFFICE
CERTIFICATE OF CORRECTION

| | |
|---|---|
| PATENT NO. | : 11,654,191 B2 |
| APPLICATION NO. | : 16/086701 |
| DATED | : May 23, 2023 |
| INVENTOR(S) | : Sno et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 0 days.

Signed and Sealed this
Twelfth Day of November, 2024

*Katherine Kelly Vidal*

Katherine Kelly Vidal
*Director of the United States Patent and Trademark Office*